United States Patent [19]

Tajiri et al.

[11] Patent Number: 5,725,601
[45] Date of Patent: Mar. 10, 1998

[54] PROCESS FOR PRODUCING WATER-ABSORBENT CROSS-LINKED, CARBOXYALKYLATED CELLULOSE-CONTAINING MATERIAL

[75] Inventors: Kozo Tajiri, Tokyo; Masayo Maeda, Kawasaki; Haruo Tsukamoto, Matsudo, all of Japan

[73] Assignee: New Oji Paper Co., Ltd., Tokyo, Japan

[21] Appl. No.: 691,098

[22] Filed: Aug. 1, 1996

Related U.S. Application Data

[63] Continuation-in-part of Ser. No. 512,223, Aug. 7, 1995, abandoned.

[30] Foreign Application Priority Data

Aug. 9, 1994 [JP] Japan ................. 6-187303

[51] Int. Cl.⁶ .............................. D04H 1/64; A61L 15/00
[52] U.S. Cl. .................. 8/120; 8/115.7; 8/116.1; 8/191; 8/193; 8/181; 8/194; 162/9; 162/157.6; 162/182; 162/146; 162/100; 162/95; 162/142; 162/148; 162/72; 162/74
[58] Field of Search ............... 8/120, 115.7, 116.1, 8/191, 193, 181, 194; 162/72, 74, 76, 77, 158, 164.3, 164.6, 164.5, 164.7, 9, 157.6, 182, 146, 100, 95, 142, 148

[56] References Cited

U.S. PATENT DOCUMENTS

| | | | |
|---|---|---|---|
| 2,137,343 | 11/1938 | Maxwell | 536/95 |
| 3,589,364 | 6/1971 | Dean et al. | |
| 3,723,413 | 3/1973 | Chatterjee et al. | 536/87 |
| 3,965,091 | 6/1976 | Holst et al. | |
| 4,136,218 | 1/1979 | Nischwitz et al. | |
| 4,248,595 | 2/1981 | Lask et al. | 8/120 |
| 5,071,681 | 12/1991 | Manning et al. | |
| 5,470,964 | 11/1995 | Qin | |

FOREIGN PATENT DOCUMENTS

| | | |
|---|---|---|
| 1020936 | 11/1977 | Canada. |
| 2223385 | 10/1974 | France. |
| 49-128987 | 12/1974 | Japan. |
| 50-85689 | 7/1975 | Japan. |
| 54-52189 | 4/1979 | Japan. |
| 54-163981 | 12/1979 | Japan. |
| 56-28755 | 3/1981 | Japan. |
| 58-1701 | 1/1983 | Japan. |
| 60-71797 | 4/1985 | Japan. |
| 60-94401 | 5/1985 | Japan. |
| 61-89364 | 5/1986 | Japan. |
| 5-253160 | 10/1993 | Japan. |
| 5-277053 | 10/1993 | Japan. |
| 5-285083 | 11/1993 | Japan. |
| 5-286100 | 11/1993 | Japan. |
| 6-17365 | 1/1994 | Japan. |
| 603 695 | 8/1978 | Switzerland. |
| 2 027 714 | 2/1980 | United Kingdom. |

OTHER PUBLICATIONS

Research Disclosure, 17060; Jun. 1978; E I du Pont de Nemours & Co., Inc. "*Composite of Synthetic–Fiber Web and Paper*".

Primary Examiner—Alan Diamond
Attorney, Agent, or Firm—Armstrong, Westerman, Hattori, McLeland & Naughton

[57] ABSTRACT

A water absorbent cross-linked, carboxyalkylated cellulose-containing material is produced by impregnating a cellulose-containing material with an aqueous reaction solution including a carboxyalkylating agent, an alkali metal hydroxide, and a cross-linking agent dissolved in water in an initial content of 50 to 90% by weight, the molar ratio of the carboxylating agent to glucose groups of cellulose being 0.7 to 2.0; adjusting the water content of the aqueous reaction solution impregnated in the cellulose-containing material to 20 to 60% by weight and of at least 5% by weight below the initial water content by evaporating a portion of water; and subjecting the water content-adjusted cellulose-containing material to a simultaneous cross-linking and carboxylating reaction procedure at 50° to 110° C., while maintaining the water content at 20 to 60% and of at least 5% by weight below the initial water content.

12 Claims, No Drawings

PROCESS FOR PRODUCING WATER-ABSORBENT CROSS-LINKED, CARBOXYALKYLATED CELLULOSE-CONTAINING MATERIAL

CROSS REFERENCE TO RELATED APPLICATION

This application is a continuation-in-part application of prior U.S. patent application Ser. No. 08/512,223, filed on Aug. 7, 1995, now abandoned.

BACKGROUND OF THE INVENTION

1. Field of the Invention

The present invention relates to a process for producing a water-absorbent cross-linked, carboxyalkylated cellulose-containing material. More particularly, the present invention relates to a process for producing a cross-linked, carboxyalkylated cellulose-containing material capable of absorbing not only water but also various aqueous solutions containing ions, for example, an aqueous common salt solution and urine, with a high degree of absorption, and thus useful as a water-absorbent material for various uses, for example, medical, sanitary, agricultural, food-packing, construction and building uses.

2. Description of the Related Art

In recent years, a group of polymeric materials referred to as super water-absorbent resins have become known as water-absorbent materials capable of absorbing water and aqueous solutions containing salts, for example, aqueous common salt solution. Basically, the super water-absorbent resins have water-insolubilized chemical structures formed by cross-linking water-soluble polymeric materials.

The super water-absorbent materials include starch derivatives produced by graft-copolymerizing acrylonitrile with starch and hydrolyzing the graft-copolymerized product, graft-polymerization products of acrylic acid metal salts, cross-linked polymers made by copolymerizing acrylic acid with a copolymerizable cross-linking agent, and hydrolysis products of methyl methacrylate-vinylacetate copolymers. Some of these are now employed in practice.

Cotton, pulp, paper, fabric and sponge, which are known as conventional water-absorbent materials, can absorb water by a capillary phenomenon. Compared with these capillary materials, the super water-absorbent resins absorb water by an osmosis phenomenon, and thus can take-up a significantly larger amount of water than the capillary materials. Also, the super water-absorbent resins have the advantage in that even when pressure is applied to the super water-absorbent resins after absorbing a large amount of water, it is very difficult to remove water from the water-absorbing resins. Accordingly, the super water-absorbent resins are widely employed for, for example, hygienic materials, for example, disposable diapers and sanitary napkins, agricultural materials, for example, soil water-retaining materials and seedbed sheets, food-related materials, for example, food freshness-keeping materials and dehydrating materials, and construction and building fields, for example, soil-retaining materials for tunneling work and water condensation-prevention sheets for buildings.

Also, various super water-absorbent materials made from cellulose derivatives are known. The cellulosic water-absorbent materials have a biodegradation property, which is not exhibited by the above-mentioned synthetic water-absorbent resins, and thus are appropriately employed in disposable sanitary materials. As a water-absorbent cellulose derivative, carboxymethyl cellulose is commonly employed. This type of water-absorbent cellulose derivative is disclosed in a number of documents, for examples, Japanese Unexamined Patent Publications (Kokai) Nos. 49-128,987, 50-85,689, 54-52,189, 54-163,981, 56-28,755, 58-1,701, 60-94,401, and 61-89,364. However, these conventional water-absorbent cellulose derivatives are disadvantageous in that the processes for producing them are complicated and costly and the resultant products exhibit a relatively low water-absorption.

For example, Japanese Unexamined Patent Publication (Kokai) No. 60-71,797 discloses a process in which a rayon filament nonwoven fabric which has been preliminarily cross-linked is wound up around a core provided with a nozzle, the wound nonwoven fabric roll is placed in a reactor vessel, and a treatment solution of sodium chloroacetate and sodium hydroxide in a mixed solvent consisting of isopropyl alcohol, methyl alcohol and water is jetted through the nozzle into the nonwoven fabric roll and permeated through the nonwoven fabric, while being heated, to convert the rayon to a carboxymethyl cellulose salt. This process is advantageous in that since a mixed solvent containing, as a principal component, aliphatic alcohols, is used, the rayon can be retained in the form of filaments during and after the carboxymethylating reaction procedure, and the resultant water-absorbent nonwoven fabric has a high softness, a satisfactory hand and a high water-absorption. However, this process is disadvantageous in that since sodium monochloroacetate and sodium hydroxide have a poor solubility in the mixed organic solvent, it is impossible to provide a treating solution containing these chemicals dissolved in a high concentration in the mixed organic solvent. Therefore, to cause a sufficient amount of the chemicals to react with the nonwoven fabric and impact a high water-absorbing property to the nonwoven fabric, a large amount of the treating solution must be brought into contact with the nonwoven fabric, and for this purpose, a specific reaction apparatus must be employed.

In another example, Japanese Unexamined Patent Publication (Kokai) No. 54-163,981 discloses a process for producing a water-swelling, cross-linked carboxyalkyl cellulose material, by a single reaction step wherein cellulose is reacted with a carboxyalkylating agent and simultaneously with a cross-linking agent in an aqueous alkaline medium. This method is applied to cellulose-based fiber materials, cellulose-based fiber-containing fiber sheet materials, and various composite sheet materials containing the cellulose-based fibers. In an initial step of this process, the fiber material or sheet material is brought into contact with a large amount of aqueous alkaline reaction mixture, and most of the reaction mixture is removed from the fiber material or sheet material so as to leave a portion of the reaction mixture in a necessary amount to complete the reaction in the fiber material or sheet material. Then the fiber material or sheet material containing the necessary amount of the reaction mixture is treated with heat energy.

This process is advantageous in that a water-absorbent material can be easily produced from a cellulose-containing material by this process. Nevertheless, this process is disadvantageous in that since in this process, a mixed aqueous solution comprising an alkali, a carboxyalkylating agent and a cross-linking agent is used, a portion of the carboxyalkylating agent is decomposed by a reaction with water at a high proportion before and during the reaction step. Therefore, the proportion of the carboxyalkylating agent effectively reacted with cellulose is reduced. Accordingly it is difficult to produce the carboxyalkylated cellulose with a high degree of substitution in a single reaction procedure. To increase the degree of substitution, the reaction procedure must be repeated twice or more. This necessity causes the reaction steps to be complicated and to become costly.

In another attempt, a water-absorbent nonwoven fabric is produced by a process in which a composite nonwoven fabric comprising synthetic fibers and cellulosic fibers is impregnated with a mixed solution containing an alkali, a carboxymethylating agent and a cross-linking agent, and then the impregnated composite nonwoven fabric is heated to convert the cellulosic fibers to cross-linked, carboxymethylated cellulose. In this process, the degree of carboxymethyl group-substitution obtained by a single reaction procedure is 0.35 to 0.48. This level of substitution is high enough to impart a satisfactory absorption of pure water to the cross-linked carboxymethyl cellulose. However, the resultant cross-linked carboxymethyl cellulose exhibits an unsatisfactory absorption of ion-containing aqueous solution, for example, isotonic aqueous sodium chloridesolution (physiologic saline). To increase the absorption of the ion-containing aqueous solution, the above-mentioned reaction procedure must be repeated twice or more to increase the degree of substitution with the carboxymethyl groups. This repetition causes the production process to be complicated and costly.

SUMMARY OF THE INVENTION

An object of the present invention is to provide a process for producing a water-absorbent cross-linked carboxyalkylated cellulose-containing material having a significantly high absorption of not only natural or tap water but also ion-containing aqueous solutions, for example, urine and aqueous common salt solutions, at a high efficiency and low cost.

The above-mentioned object can be attained by the process of the present invention for producing a water-absorbent cross-linked carboxyalkylated cellulose-containing material, comprising the steps of:

impregnating a cellulose-containing material with an aqueous reaction solution containing a carboxyalkylating agent, an alkali metal hydroxide, and a cross-linking agent for cellulose and having an initial water content of 50 to 90% by weight, in the impregnated aqueous reaction solution, the carboxyalkylating agent being present in a molar ratio to glucose groups of cellulose in the cellulose-containing material, of 0.7 to 2.0.

adjusting the water content of the aqueous reaction solution impregnated in the cellulose-containing material to a level of from 20 to 60% by weight and of at least 5% by weight below the initial water content, by evaporating away a portion of water from the impregnated aqueous reaction solution; and subjecting the resultant aqueous reaction solution-impregnated cellulose-containing material to a simultaneous carboxyalkylating and cross-linking reaction procedure by heating it at a temperature of 50° to 110° C., while maintaining the water content in the impregnated aqueous reaction solution at the level of 20 to 60% by weight and of at least 5% by weight below the initial water content, to convert cellulose in the cellulose-containing material to cross-linked, carboxyalkylated cellulose.

In the process of the present invention, the cellulose-containing material may be selected from the group consisting of cellulose fiber materials and mixed fiber materials comprising cellulose fibers and synthetic fibers.

The cellulose-containing materials are preferably in the form of a sheet.

Preferably, the resultant cross-linked, carboxyalkylated cellulose has a degree of substitution with carboxyalkyl groups of 0.35 to 0.8.

DESCRIPTION OF THE PREFERRED EMBODIMENTS

The inventors of the present invention made an extensive study into imparting an enhanced absorption of not only natural or tap water but also ion-containing aqueous solutions to cellulose. As a result, the inventors found that a carboxyalkylating agent, alkali metal hydroxide and cross-linking agent can be dissolved each only at a certain upper limit of concentration or less in water, and thus the water content in the resultant aqueous reaction solution must be maintained at a level not lower than a certain lower limit. In other words, in a practical aqueous reaction solution, the carboxyalkylating agent, the alkali metal hydroxide and the cross-linking agent are present in a low concentration and thus the reaction rate of these chemicals with cellulose is not satisfactory and the degree of substitution with a carboxyalkyl group obtainable by one single reaction procedure is not so high.

The inventors further found that the above-mentioned disadvantage of the aqueous reaction solution can be removed by adjusting after impregnating a cellulose-containing-material with an aqueous reaction solution, the water content in the aqueous reaction solution impregnated in the cellulose-containing material to a reduced level by evaporating away a portion of the water contained in the aqueous reaction solution, so as to increase the concentrations of the chemicals in the impregnated aqueous reaction solution and restrict the decomposition of the carboxyalkylating agent with water, and then reacting the chemicals in the aqueous reaction solution with cellulose. Furthermore, the inventors found that by the above-mentioned reduction in the water content of the impregnated aqueous reaction solution, the degree of the carboxyalkyl group-substitution is enhanced even in one single reaction procedure, and the resultant cross-linked, carboxyalkylated cellulose exhibits a high absorption of not only natural or tap water but also ion-containing aqueous solutions, for example, urine or aqueous common salt solutions. The present invention was completed based on the above-mentioned discovery of the inventors.

In the process of the present invention, the cellulose-containing material may be in the form of fibers, filaments, yarns, threads fiber sheets including woven fiber sheets, knitted fiber sheets and non-woven fiber sheet, sponges or films.

The cellulose fibers usable for the present invention may include wood pulp fibers made from woods, non-wood pulp fibers made from herbage plants and regenerated cellulose fibers.

The pulp fibers made from woods include chemical pulp fibers which are produced from soft wood chips or hard wood chips by a kraft pulping method, sulfite pulping method, soda pulping method, or polysulfide pulping method; mechanical pulp fibers which are made by mechanically pulping wood chips or logs by using a refiner or grinder; semi-chemical pulp fibers made by pre-treating wood chips with a chemical reactant and then mechanically pulping the pre-treated wood chips; and secondary (recycled) paper pulp fibers recovered from waste newspaper, waste fine paper, and used office paper. The pulp fibers as mentioned above may be bleached or non-bleached.

The non-wood pulp fibers made from the herbage plants include those made by pulping cotton fibers, manila hemp fibers, flax fibers, straw fibers, bamboo fibers, bagasse fibers, kenaf fibers, Kozo (paper mulberry) fibers and Mitsumata fibers by a pulping method similar to that applied to the wood chips.

The regenerated cellulose fibers include viscose rayon fibers which are produced by converting cellulose material to a viscose solution, spinning the viscose solution and solidify-regenerating the filamentary viscose solution streams in an acid solution; copper-ammonia rayon fibers which are produced by dissolving a cellulose material in a copper-ammonia solution, spinning the resulting cellulose solution and solidify-regenerating the filamentary cellulose solution streams in an acid solution; and other regenerated cellulose fibers produced, for example, by dissolving a cellulose material in a non-aqueous solvent, for example, N-methylmorpholine-N-oxide and converting the resultant solution to fibers. The sheet-formed cellulose materials include paper sheets, regenerated cellulose fiber, rayon fabrics, cotton fabrics, linen fabrics, and fabrics made from mixed fiber yarns containing cotton or linen fibers and synthetic fibers.

The cellulose-containing nonwoven fiber sheets include continuous rayon filament nonwoven fabrics, cotton nonwoven fabrics made by a water jet entangling method, wood pulp nonwoven fabrics made by an air jet method or rayon staple fiber nonwoven fabrics made by a carding method.

The cellulose sponges usable for the present invention can be produced by foaming a viscose solution and regenerating the foamed viscose solution by rinsing it with an acid solution.

In the process of the present invention, the cellulose-containing material may be a composite nonwoven fabric which is made from synthetic fibers and cellulose fibers by bonding them to each other through a hot melt bonding agent or by intertwining these fibers with each other by a water-jet fiber-entangling method. In the composite nonwoven fabric, the synthetic fibers may be selected from common synthetic fibers, for example, polyolefin fibers, polyester fibers, polyamide fibers, polyacrylate fibers and polyurethane fibers. The synthetic fibers may be employed in the form of a fiber mass, or a sheet, namely a nonwoven fabric.

The synthetic fibers preferably have a thickness of 0.33 to 1.11 d tex (0.3 to 10 denier). If the thickness is more than 1.11 d tex (10 denier), the resultant nonwoven fabric has a low softness and thus, when the synthetic fibers are incorporated together with water-absorbent cellulose fibers into the water-absorbent material, the resultant water-absorbent material may exhibit unsatisfactory softness, hand and processability. Also, if the thickness is less than 0.33 d tex (0.3 denier), the resultant nonwoven fabric may exhibit a high density and a paper-like stiff hand and thus it is difficult to control the properties of the nonwoven fabric.

The process for producing a composite sheet from synthetic fibers and cellulose fibers may be selected from conventional processes, for example, the processes disclosed in "Research Disclosure, 17060, June 1978", and Japanese Unexamined Patent Publications (Kokai) Nos. 5-253,160, 5-277,053, 5-285,083, 5-286,100, and 6-17,365. In the processes disclosed in these documents, a synthetic fiber nonwoven fabric and a paper sheet are laminated on each other and water-jet fiber-entangling method is applied to the laminate to intertwine the synthetic fibers with the cellulose fibers. The resultant composite nonwoven fabric exhibits satisfactory hand and processability, and thus is useful as a starting material for the process of the present invention. In this case, the synthetic fiber nonwoven fabric must have a mechanical strength high enough to resist the water jet pressure. Therefore, the synthetic fiber nonwoven fabric is preferably made from continuous synthetic filaments.

The cellulose-containing material usable for the process of the present invention may be a composite staple fiber nonwoven fabric made by blending of synthetic staple fibers with cellulose staple fibers and forming the fiber blend into a nonwoven fabric by a wet or dry nonwoven fabric-forming method. In this case, to enhance the wet mechanical strength of the resultant composite nonwoven fabric, the synthetic fibers are partially bonded to each other through a conventional bonding method. In the conventional partial bonding method, a hot melt binder powder is distributed throughout the synthetic fiber web and heated so as to partially bond the fibers to each other through the hot melted binder. In another method, the synthetic fibers are blended with hot melt bonding fibers and the fiber blend is formed into a nonwoven fabric and heated so as to partially bond the synthetic fibers to each other through the hot-melted bonding fibers. In still another method, the synthetic fibers or filaments are formed into a nonwoven fabric by a needle-punching method or stitch-bonding method.

An example of the cellulose-containing composite sheet usable for the process of the present invention can be produced by laminating a paper sheet prepared from cellulose fibers consisting of wood pulp by a conventional wet paper-forming machine on a nonwoven fabric made from synthetic continuous filaments; and spouting high pressure water jet streams toward the paper sheet layer of the laminate so that the water jet streams penetrate to the synthetic filament nonwoven fabric layer through the paper sheet layer, and the cellulose fibers and synthetic filaments are intertwined with each other. In the preparation of the composite sheet, the cellulose fibers and the synthetic filaments are preferably employed in a weight ratio of the cellulose fibers to the synthetic filaments of 1:1 to 19:1. If the weight ratio is less than 1:1, the content of the cellulose fiber in the composite sheet may be too small and thus the resultant water-absorbent material may exhibit an unsatisfactory water-absorption. Also, if the weight ratio is more than 19:1, the cellulose fibers may be difficult to fully intertwine with the synthetic filaments, and thus when the resultant water-absorbent composite material is brought into contact with water, the resultant water-absorbent cellulose derivative fibers swollen with water may be easily removed from the composite material, and the water-absorbed composite material may exhibit a poor wet tensile strength.

To produce the water-absorbent material from the cellulose-containing material in accordance with the process of the present invention, the cellulose containing material is impregnated with an aqueous reaction solution containing a carboxyalkylating agent, an alkali metal hydroxide and a cross-linking agent for cellulose.

Preferably, the aqueous reaction solution contains 7 to 30% by weight more preferably 14 to 28% by weight, of a carboxyalkylating agent, 2.5 to 15% by weight, more preferably 5 to 14% by weight, of an alkali metal hydroxide and 0.5 to 5% by weight, more preferably 1 to 3% by weight, of a cross-linking agent.

In the impregnating step, the initial water content of the aqueous reaction solution is 50 to 90% by weight preferably 55 to 80% by weight. Also the aqueous reaction solution contains the carboxyalkylating agent in a molar ratio to glucose groups of cellulose in the cellulose-containing material of 0.7 to 2.0.

Then, the water content of the aqueous reaction solution impregnated in the cellulose-containing material is reduced and adjusted to a level of from 20 to 60% by weight and at least 5% below the initial water content, by evaporating away a portion of water from the impregnated aqueous reaction solution.

For example, when the initial water content is 60% by weight, the water content of the aqueous reaction solution impregnated in the cellulose-containing material must be reduced and adjusted to a level within the range of from 20 to 55% by weight. Also, when the initial water content is 50% by weight, the adjusted water content must be within the range of from 20 to 45% by weight.

Further, when the initial water content is in a range of from 65 to 90% by weight the water content must be reduced and adjusted to the range of from 20 to 60% by weight.

Next, the resultant cellulose-containing material impregnated with the aqueous reaction solution is subjected to a simultaneous carboxyalkylating and cross-linking reaction procedure by heating it at a temperature of 50° to 110° C. During the reaction procedure, the water content of the impregnated aqueous reaction solution is maintained at a level of 20 to 60% by weight and at least 5% by weight below the initial water content, to smoothly carboxyalkylate and cross-link the cellulose in the cellulose-containing material.

The carboxyalkylating agent comprises at least one alkali metal salt of aliphatic monohaloalkylcarboxylic acids preferably having 2 or 3 carbon atoms. The alkali metal salts of aliphatic monohaloalkylcarboxylic acids include alkali metal monochloro-acetates, alkali metal monobromoacetates, alkali metal α-chloropropionates, alkali metal β-chloropropionates, alkali metal α-bromopropionates and alkali metal β-bromopropionates. These compounds may be employed alone or in a mixture of two or more thereof. Most preferably sodium monochloroacetate is used because of the low price thereof.

The alkali metal hydroxide is selected from sodium hydroxide and other alkali metal hydroxides, for example, lithium hydroxide, potassium hydroxide, rubidium hydroxide, and cesium hydroxide. The most preferable alkali metal hydroxide is sodium hydroxide.

The cross-linking agent comprises at least one cross-linking compound capable of cross-linking cellulose in an alkaline aqueous reaction solution, having a boiling point as high as possible and being substantially nonvolatile under the reaction conditions.

The process of the present invention includes the procedure of evaporating away a portion of the water in the aqueous reaction solution impregnated in the cellulose-containing material. Accordingly, it is necessary that during the water-evaporating procedure, the cross-linking agent evaporate as little as possible. Therefore, a cross-linking agent, which has a low boiling temperature and a high volatility is not suitable for the process of the present invention.

The cross-linking agent usable for the present invention preferably comprises at least one member selected from the group consisting of polyepoxy compounds, for example, ethyleneglycol diglycidylether, glycerol diglycidylether, glycerol triglycidylether, polyethyleneglycol diglycidylether, and diepoxybutane; divinyl compounds, for example, divinyl sulfone and methylene bisacrylamide; polyhalo compounds, for example, dichloropropyle alcohol, dibromopropyl alcohol and dichloroacetic acid; and polyaziridinyl compounds, for example, tetramethylolmethane-tri-β-aziridinylpropionate and trimethylolpropane-tri-β-aziridinylpropionate. The above-mentioned cross-linking compounds may be used alone or in a mixture of at least two thereof. Epichlorohydrin, which is commonly employed as a cross-linking agent for cellulose derivatives, and can impart a high pure water-absorbing property to the cellulose derivatives, has a low boiling temperature and thus is not appropriate for the process of the present invention. Preferably, the cross-linking agent has a boiling temperature of about 200° C. or more.

In the preparation of the aqueous reaction solution, the carboxyalkylating agent, the alkali metal hydroxide and the cross-linking agent are dissolved in water. The initial water content of the aqueous reaction solution is variable depending on the solubility of the carboxyalkylating agent or the alkali metal hydroxide in water. However, the initial water content should be as low as possible as long as the chemicals can be fully dissolved in water. Namely, the initial water content of the aqueous reaction solution is controlled to a level of from 60 to 90% by weight. If the initial water content is more than 90% by weight, in the next water content-adjusting step, a large amount of water must be evaporated away with a high energy cost. Also, if the initial water content is less than 60% by weight, some of the chemicals may not be completely dissolved in the aqueous reaction solution, and thus may not be evenly impregnated in the cellulose-containing material.

In the aqueous reaction solution, preferably, the molar ratio of the alkali metal hydroxide to the carboxyalkylating agent is 0.8 to 1.2, more preferably 1.0 to 1.1. If the molar ratio is less than 0.8 or more than 1.2, some of the chemicals are left unreacted, and thus reaction efficiency of the chemicals becomes low.

The content of the cross-linking agent in the aqueous reaction solution is variable in response to the type of the cross-linking agent and the reaction conditions, and is preferably controlled to 1.5 to 15%, more preferably 3 to 9%, based on the weight of cellulose contained in the cellulose-containing material.

In the process of the present invention, the molar ratio of the carboxyalkylating agent contained in the aqueous reaction solution to glucose groups of cellulose contained in the cellulose-containing material is 0.7 to 2.0, preferably 1.0 to 1.5. If the molar ratio is less than 0.7, it is difficult to obtain carboxyalkylated, cross-linked cellulose having a degree of substitution of 0.35 or more, and thus the resultant carboxylated, cross-linked cellulose exhibits an unsatisfactory water-absorption. Also, if the molar ratio is more than 2.0, this high molar ratio substantially does not contribute to increasing the degree of substitution with the carboxylalkyl groups and causes an economical disadvantage.

The degree of substitution can be increased by repeating the process of the present invention twice or more so as to increase the total molar ratio of the carboxyalkylating agent to the glucose groups. However, the repetition is economically disadvantageous.

There is no limitation to the impregnation method of the cellulose-containing material with the aqueous reaction solution. Usually, the cellulose-containing material is immersed in a large amount of the aqueous reaction solution, squeezed between squeezing rollers to remove an excessive amount of aqueous reaction solution, and to adjust the initial water content of the aqueous reaction solution impregnated in the cellulose-containing material to a desired level. Where the cellulose-containing material is in the form of a sheet, the aqueous reaction solution is coated in a predetermined amount on one or both surfaces of the cellulose-containing sheet by a coater.

Where the cellulose-containing material is in the form of a cut (staple) fiber mass, the cut fiber mass may be placed in a kneader and mixed with a predetermined amount of the aqueous reaction solution in the kneader.

After the impregnating step is completed the aqueous reaction solution-impregnated cellulose-containing material is subjected to the water content-adjusting step in which a portion of water in the aqueous reaction solution impregnated in the cellulose-containing material is evaporated away, to adjust the water content of the impregnated aqueous reaction solution to a level of at least 5% by weight below the initial water content and in the range from 20 to 60% by weight. The evaporating procedure is carried out, for example, by blowing hot air along or toward the cellulose-containing material at a temperature of, for example, 50° to 150° C. for a necessary time, for example, several seconds to several minutes. There is no limitation on the evaporating method. Nevertheless, the evaporation should be completed within as short a time as possible. Since the carboxyalkylating reaction rate with cellulose is considerably high, if the evaporation procedure is carried out over too long a time, for example, 30 minutes or more, even at the above-mentioned temperature, the carboxyalkylating reaction is undesirably carried out or completed during the evaporating procedure, and thus, the specific advantage of the process of the present invention cannot be obtained. Accordingly, the water content-adjusting step should be completed before the carboxyalkylating reaction with cellulose substantially does not start. Namely, in the water content-adjusting step, the degree of substitution by carboxyalkyl group is preferably restricted to 0.1 or less. For this purpose, the water content-adjusting step is carried out in a dryer or reactor by blowing hot air at a temperature of from 40° C. to 150° C. for a time not longer than 30 minutes. In this water content-adjusting step, if the adjusted water content is lower than 20% by weight, the degree of substitution becomes significantly low, and the cellulose-containing material is discolored yellow. Also, if the adjusted water content is higher than 60% by weight, the specific advantage of the process of the present invention cannot be obtained. Further, if the reduction in the water content from the initial level thereof is smaller than 5% by weight, the specific advantage of the process of the present invention becomes unsatisfactory.

In the process of the present invention, immediately after the water content-adjusting step is completed, substantially no carboxyalkylating reaction with cellulose occurs. Then, the aqueous reaction solution-impregnated and water content-adjusted cellulose-containing material is subjected to a simultaneous carboxyalkylating and cross-linking reaction procedure at a temperature of 50° to 110° C. In the reaction procedure, the water content of the aqueous reaction solution impregnated in the cellulose-containing material is maintained at a level of 20 to 60% by weight.

If the reaction temperature is lower than 50° C., the reaction time necessary to complete the reaction becomes too long. Also, if the reaction temperature is higher than 110° C., the resultant carboxyalkylated cellulose exhibits a low degree of substitution and an unsatisfactory water absorption, and sometimes becomes a significantly discolored yellow.

If the water content becomes less than 20% by weight, the resultant carboxyalkylated cellulose has an unsatisfactory degree of substitution and is discolored yellow.

The reaction step may be carried out continuously by conveying the aqueous reaction solution-impregnated cellulose-containing material through a heat-reactor, or batchwisely by heating the material in a closed reactor.

In the reaction step, the aqueous reaction solution-impregnated cellulose-containing material may be heated by an external heating method. Where the cellulose-containing material has a high cellulose content, since the carboxyalkylating reaction is exothermic, sometimes the cellulose-containing material naturally reaches the desired temperature. In this case, the reaction procedure can be naturally conducted in a closed reactor or opened reactor without external heating.

The time necessary to complete the reaction is variable in response to the reaction temperature and the type of reactor. Usually, the reaction is completed within 10 minutes to 4 hours. If the reaction time is shorter than 10 minutes, the reaction may not be completed. Also, a reaction time longer than 4 hours is economically disadvantageous, because the reaction is completed within 4 hours.

The pure water-absorption of the cross-linked, carboxyalkylated cellulose is established mainly in response to the degree of carboxyalkyl group-substitution and the density of cross-linkage. Theoretically, the higher the degree of carboxyalkyl group-substitution, the higher the pure water-absorption of the carboxyalkylated cellulose. Practically, the process of the present invention is carried out to such an extent that the degree of carboxyalkyl group-substitution reaches 0.35 to 0.8, by one application of the process. The practical upper limit of the degree of carboxyalkyl group-substitution on cellulose is about 1.2. Even if the substitution degree is increased to more than 1.2, the water absorption of the resultant carboxyalkylated cellulose is substantially saturated. Also, the degree of carboxyalkyl group-substitution of more than 0.8 can be obtained only by repeating the process of the present invention twice or more. The repetition of the process causes the total process to be complicated and too costly.

If the degree of carboxyalkyl group-substitution is less than 0.35, the resultant carboxyalkylated cellulose exhibits an unsatisfactory water absorption.

Since the degree of caboxyalkyl group-substitution is variable in response to the molar ratios of the carboxyalkylating agent and the alkali metal hydroxide to the glucose groups of cellulose, the adjusted water content of the aqueous reaction solution impregnated in the cellulose-containing material, the reaction temperature and the reaction time, and the desired degree of carboxyalkyl group-substitution can be established by controlling the above-mentioned features or combinations of the features.

Also, in the cross-linked, carboxyalkylated cellulose, the lower the density of cross-linkage, the higher the pure water-absorption. If the cross-linkage density is too low, the resultant water-absorbed carboxyalkylated cellulose gel exhibits a low mechanical strength, and a water-soluble fraction of the carboxyalkylated cellulose salt is eluted in water so that the water-absorbed carboxyalkylated cellulose gel becomes sticky or adhesive.

If the cross-linkage density is too high, the resultant cross-linked, carboxyalkylated cellulose exhibits an unsatisfactory water absorption. Accordingly, the cross-linkage density should be established in consideration of the desired water absorption and use of the cross-linked, carboxyalkylated cellulose-containing material. The cross-linkage density can be controlled by controlling the amount of the cross-linking agent in the aqueous reaction solution applied to the cellulose-containing material.

After the reaction step is completed, the resultant reaction product contains a large amount of impurities including inorganic salts and decomposition residue of the carboxyalkylating agent. Accordingly, the reaction product is refined to remove the impurities. The refining procedure can be effected by a conventional method. For example, the reaction product is rinsed with a cleaning liquid comprising water and at least one organic solvent compatible with water, for example, aliphatic lower alcohols such as methyl alcohol, ethyl alcohol and isopropyl alcohol, and then dried.

In view of the conventional process for producing a cross-linked carboxyalkylated cellulose-containing material by impregnating a cellulose-containing material with an aqueous reaction solution containing a cross-linking agent, a carboxyalkylating agent and an alkali metal hydroxide, and heating the impregnated cellulose-containing material to simultaneously cross-link and carboxyalkylate cellulose, the process of the present invention has an essential step of adjusting a water content of the aqueous reaction solution impregnated in the cellulose-containing material to a specific level of 20 to 60% by weight and of at least 5% by weight below the initial water content of the aqueous reaction solution, by evaporating away a portion of water contained in the initially impregnated aqueous reaction solution.

By the essential water content-adjusting step, the simultaneous cross-linking and carboxyalkylating reaction procedure can be effected at derived concentrations of the chemicals which are higher than the initial concentrations of the chemicals in the aqueous reaction solution. Therefore, the simultaneous cross-linking and carboxyalkylating reaction procedure can be conducted in a high efficiency and undesired hydrolysis of the carboxyalkylating agent can be restricted. In other words, the expensive carboxyalkylating agent can be effectively utilized and the reaction cost can be reduced. Further, an increase in the concentration of the alkali metal hydroxide in the aqueous reaction solution impregnated in the cellulose-containing material can promote the formation of alkali cellulose which has an enhanced reactivity with the carboxyalkylating agent and the cross-linking agent.

Also, the water content-adjusting step is contributory to enhancing the degree of carboxyalkyl group-substitution of cellulose, and thus a desired substitution degree can be obtained with only one application of the process of the present invention, without repeating the process application. Therefore, the process of the present invention enables the cross-linked, carboxyalkylated cellulose-containing material to have a satisfactory absorption of not only pure water but also ion-containing aqueous solutions to be produced at a high efficiency and low cost.

EXAMPLES

The present invention will be further explained by the following specific examples which are merely representative and do not restrict the scope of the present invention in any way.

In the examples and comparative examples, (1) pure water absorption, (2) isotonic sodium chloride solution absorption, and (3) degree of carboxyalkyl group substitution of cross-linked, carboxyalkylated cellulose are determined by the methods as described below.

(1) Pure water absorption

Pure water was prepared by deionizing water by flowing through an ion-exchange resin and distilling the deionized water.

A specimen having a weight of 1 g was placed in a 250 mesh nylon wire bag having dimensions of 10 cm×10 cm. The specimen-containing nylon wire bag was immersed in the pure water at a temperature of 25° C. for 10 minutes to allow the specimen to absorb the pure water, and was then removed from the pure water and suspended for 10 minutes to allow a portion of the pure water to drip down. Then the weight of the water-absorbed specimen was measured.

The water absorption of the specimen was represented by the weight of pure water retained in the specimen per g of the dry weight of the specimen.

(2) Isotonic sodium chloride solution absorption

The same measurement procedures as for the pure water absorption were carried out, except that the pure water was replaced by an aqueous solution of 0.9% by weight of NaCl.

(3) Degree of carboxyalkyl group substitution

A carboxymethylated cellulose specimen (Examples 1 to 5) having a weight of 1 g was placed in a flask, and a methyl alcohol-hydrogen chloride-mixed aqueous solution prepared by dissolving hydrogen chloride in an aqueous solution of 70% by volume of methyl alcohol and having a concentration of hydrogen chloride of 1 mole/liter was added in an amount of 50 ml into the flask. The resultant reaction system was left standing at room temperature for one hour. Then, the specimen was removed from the methyl alcohol-hydrogen chloride mixed aqueous solution, fully rinsed with methyl alcohol to completely remove hydrogen chloride from the specimen, and dried at room temperature.

The dried specimen was placed in an Erlenmeyer flask having an inside volume of 300 ml, 50 ml of 0.1N sodium hydroxide aqueous solution and 100 ml of pure water were placed in the flask, and the content in the flask was slowly stirred for one hour. Thereafter, the degree of substitution of the cellulose with carboxymethyl groups was determined by titration using a titrant consisting of 0.1N hydrochloric acid aqueous solution and an indicator consisting of phenolphthalein, in accordance with the following equations (1) and (2):

$$Y = 0.1A - 0.1B \qquad (1)$$

$$\text{Substitution degree} = 162Y/(1000W - 80Y) \qquad (2)$$

wherein A represents an amount in ml of the 0.1N sodium hydroxide aqueous solution, B represents an amount in ml of the 0.1N hydrochloric acid aqueous solution, Y represents the amount in milli equivalent of carboxymethyl groups and W represents a weight in g of the water absorbent carboxymethylated cellulose sodium salt.

When the specimen consisted of a methylcarboxymethylated cellulose sodium salt (Example 6), the degree of substitution with methylcarboxymethyl groups was calculated in accordance with the following equation (3):

$$\text{Degree of substitution} = 162Y'/(1000W' - 94Y') \qquad (3)$$

wherein Y' represents the amount in milli equivalent of methylcarboxymethyl groups and W' representing the water absorbent methylcarboxymethylated cellulose sodium salt.

Example 1

A cellulose fiber-containing composite sheet was prepared by laminating a paper sheet having a basis weight of 76 g/m² and prepared from soft wood bleached kraft pulp, on a spun-bonded nonwoven fabric prepared from polypropylene continuous filaments with a thickness of 2.78 d tex (2.5 denier) and having a basis weight of 12 g/m², and spouting water jet streams under high pressure toward the paper sheet layer of the laminate so that the spouted water jet streams penetrated into the spun-bonded nonwoven fabric layer through the paper sheet layer and the pulp fibers and the polypropylene filaments were intertwined with each other by the water jet streams.

The resultant composite sheet had a basis weight of 80 g/m².

The composite sheet was cut into pieces each having dimensions of 20 cm×30 cm and a weight of 4.8 g. The cut pieces were immersed in an aqueous reaction solution comprising 8.38% by weight of sodium hydroxide, 24.4% by weight of sodium monochloroacetic acid, 0.68% by weight of ethyleneglycol diglycidylether and 66.54% by weight of water, at room temperature for one minute. Then the cut pieces were removed from the aqueous reaction solution, interposed and pressed between filtering paper sheets, to adjust the amount of the aqueous reaction solution impregnated in the cut pieces to 3 g per g of the absolute dry weight of the pieces. In the aqueous reaction solution-impregnated composite sheet pieces, a molar ratio of the carboxymethylating agent to glucose groups was 1.3/1.

A hot air dryer with an electric heater and a ventilator was preheated to a temperature of 50° C., the aqueous reaction solution-impregnated composite sheet pieces were placed in the dryer for 5 minutes while ventilating to evaporate away a portion of water from the impregnated aqueous reaction solution. After the pieces were removed from the dryer, the water content of the impregnated aqueous reaction solution was 42% by weight. The water content-adjusted pieces were immediately placed in a polyethylene sheet bag and sealed so as to prohibit the evaporation of water from the impregnated aqueous reaction solution. The bag was placed in the dryer and heated at a temperature of 50° C. for 3 hours to cross-link and carboxymethylate the pulp fibers in the pieces.

Then, the composite sheet pieces removed from the dryer were immersed in a 70% methyl alcohol aqueous solution, removed from the aqueous solution, and interposed and pressed between filtering paper sheets. These procedures were repeated four times to fully rinse the pieces. Finally, the rinsed pieces were further immersed in pure methyl alcohol, removed therefrom, interposed and pressed between filtering paper sheets, and dried in the ambient air atmosphere.

The resultant cross-linked, carboxymethylated cellulose-containing composite sheet pieces were subjected to the above-mentioned tests.

The test results are shown in Table 1.

Example 2

The same procedures as in Example 1 were carried out except that the composite sheet comprising pulp fibers and polypropylene filaments intertwined with each other by a water jet entangling method, having a basis weight of 80 g/m² and impregnated with the aqueous reaction solution was heated in the dryer at 50° C. for one minute, to adjust the water content in the impregnated aqueous reaction solution to 58% by weight.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

Example 3

The same procedures as in Example 1 were carried out except that the composite sheet comprising pulp fibers and polypropylene filaments intertwined with each other by a water jet entangling method, having a basis weight of 80 g/m² and impregnated with the aqueous reaction solution was heated in the dryer at 50° C. for 7 minutes, to adjust the water content in the impregnated aqueous reaction solution to 22% by weight.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

Example 4

A soft wood kraft pulp in an amount of 20 g was divided into small pieces and charged into a double arm type kneader (Type: S1-1, made by Moriyama Seisakusho, arm revolution rate: 60 rpm or 100 rpm) and mixed with 60 g of an aqueous reaction solution consisting of 8.38% by weight of sodium hydroxide, 24.40% of weight of sodium monochloroacetate, 0.68% by weight of ethyleneglycol diglycidylether and 66.54% by weight of water, and having a molar ratio of the carboxymethylating agent to glucose groups in the pulp fibers of 1.1/1. The content in the kneader was fully mixed for 10 minutes. The mixture was pulverized by using a home mixer to form a fibrous mass.

The fibrous mass was spread in the form of a thin web on a stainless steel plate and dried in the same dryer as in Example 1 at a temperature of 60° C. for 3 minutes while ventilating. The water content of the aqueous reaction solution impregnated in the pulp fibers was adjusted to 45% by weight.

The water content adjusted fibrous mass was placed and sealed gas-tight in a polyethylene bag to prohibit the evaporation of water from the impregnated aqueous reaction solution. The bag was placed in the dryer and heated at a temperature of 60° C. for 2 hours. After the reaction procedure was completed, the resultant fibrous mass was placed and stirred in a 70% methyl alcohol aqueous solution at room temperature for one hour, and filtered through a glass filter (2G). The fibrous mass on the glass filter was fully rinsed with 2000 ml of a 70% methyl alcohol aqueous solution, then with 500 ml of 100% methyl alcohol, and dried under vacuum. A water-absorbent cellulose derivative material was obtained.

The resultant water-absorbent cellulose derivative material was subjected to the above-mentioned tests for the pure water absorption, the isotonic sodium chloride solution absorption and the degree of the carboxymethyl group substitution.

The test results are shown in Table 1.

Example 5

A paper sheet made from 80% by weight of hard wood kraft pulp and 20% by weight of soft wood kraft pulp and having a basis weight of 64 g/m² was cut into pieces each with dimensions of 20 cm×30 cm and an absolute dry weight of 3.84 g.

The cut paper sheets were immersed in an aqueous reaction solution consisting of 11.99% by weight of potassium hydroxide, 24.95% by weight of sodium monochloroacetate, 1.23% by weight of ethyleneglycol diglycidylether and 61.83% by weight of water, at room temperature for one minute, removed from the aqueous reaction solution and interposed and pressed between filtering paper sheets, to adjust the amount of the aqueous reaction solution impregnated in the paper sheet to 3 g per g of the absolute dry weight of the paper sheet. The molar ratio of the carboxymethylating agent to glucose groups of the paper sheet was 1.1/1.

The same hot air dryer as in Example 1 equipped with an electric heater and a ventilator was preheated at a temperature of 50° C., and the aqueous reaction solution-impregnated paper sheets were placed in the dryer and heated at 50° C. for 5 minutes while ventilating, to evaporate a portion of the water in the impregnated aqueous reaction solution and to adjust the water content in the impregnated aqueous reaction solution to 30% by weight.

Thereafter, the water content-adjusted paper sheets were removed from the dryer, placed and tightly sealed in a polyethylene bag to prohibit the evaporation of water. The bag was placed in the dryer and heated at 50° C. for 3 hours to cross-link and carboxymethylate the paper sheets in the bag.

The resultant paper sheets removed from the bag were immersed in a 70% methyl alcohol aqueous solution at room temperature and interposed and pressed between filtering paper sheets. The above-mentioned treatments were repeated four times to fully rinse the paper sheets. Then the paper sheets were immersed in 100% methyl alcohol, removed therefrom, interposed and pressed between filtering paper sheets, and dried in the ambient air atmosphere. A water-absorbent cellulose derivative material was obtained.

The water-absorbent cellulose derivative material was subjected to the above-mentioned tests for the pure water absorption, the isotonic sodium chloride solution and the degree of carboxymethyl group substitution.

The test results are shown in Table 1.

Example 6

The same composite sheet as in Example 1 comprising pulp fibers and polypropylene filaments intertwined with each other by a water jet entangling method and having a basis weight of 80 g/m$^2$, was immersed in an aqueous reaction solution consisting of 8.40% by weight of sodium hydroxide, 27.39% by weight of sodium α-chloropropionate, 0.76% by weight of ethyleneglycol diglycidylether and 63.45% by weight of water, at room temperature for one minute, removed from the aqueous reaction solution and interposed and pressed between filtering paper sheets, to adjust the amount of the aqueous reaction solution impregnated in the paper sheet to 3.9 g per g of the absolute dry weight of the paper sheet. The molar ratio of the methylcarboxymethylating agent to glucose groups of the paper sheet was 1.7/1.

The same hot air dryer as in Example 1 equipped with an electric heater and a ventilator was preheated at a temperature of 50° C., and the aqueous reaction solution-impregnated paper sheets were placed in the dryer and heated at 50° C. for 4 minutes while ventilating, to evaporate a portion of water in the impregnated aqueous reaction solution and to adjust the water content in the impregnated aqueous reaction solution to 26% by weight.

Thereafter, the water content-adjusted paper sheets were removed from the dryer, placed and tightly sealed in a polyethylene bag to prohibit the evaporation of water. The bag was placed in the dryer and heated at 50° C. for 3 hours to cross-link and carboxymethylate the paper sheets in the bag.

The resultant paper sheets removed from the bag were immersed in a 70% methyl alcohol aqueous solution at room temperature and interposed and pressed between filtering paper sheets. The above-mentioned treatments were repeated four times to fully rinse the paper sheets. Then the paper sheets were immersed in 100% methyl alcohol, removed therefrom, interposed and pressed between filtering paper sheets, and dried in the ambient air atmosphere. A water-absorbent cellulose derivative material was obtained.

The water-absorbent cellulose derivative material was subjected to the above-mentioned tests for the pure water absorption, the isotonic sodium chloride solution and the degree of methylcarboxymethyl group substitution.

The test results are shown in Table 1.

Comparative Example 1

The same procedures as in Example 1 were carried out except that the composite sheet comprising pulp fibers and polypropylene filaments intertwined with each other by a water jet entangling method, having a basis weight of 80 g/m$^2$ and impregnated with the aqueous reaction solution was directly placed and sealed in the polyethylene bag, without applying the water content adjusting step, and the bag was heated in the dryer at a temperature of 50° C. for 3 hours.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

Comparative Example 2

The same composite sheet as in Example 1 comprising pulp fibers and polypropylene filaments intertwined with each other by a water jet entangling method, and having a basis weight of 80 g/m$^2$ was impregnated with the same aqueous reaction solution as in Example 6, placed and sealed in the polyethylene bag and directly subjected to the reaction procedure without applying the water content-adjusting step.

The resultant cross-linked, carboxymethylated cellulose-containing composite sheet was subjected to the above-mentioned tests for the pure water absorption, the isotonic sodium chloride solution absorption and the degree of methylcarboxymethyl group substitution.

The test results are shown in Table 1.

Comparative Example 3

The same composite sheet as in Example 1 comprising pulp fibers and polypropylene filaments intertwined with each other by a water jet entangling method, and having a basis weight of 80 g/m$^2$ was impregnated with an aqueous reaction solution consisting of 10.4% by weight of sodium hydroxide, 34.6% by weight of potassium monochloroacetate, 1.0% by weight of epichlorohydrine, and 54.0% by weight of water at room temperature for one minute. The paper sheet was removed from the aqueous reaction solution, and interposed and pressed between filtering paper sheets to adjust the amount of the aqueous reaction solution impregnated in the composite sheet to 2.4 g per g of the absolute dry weight of the composite sheet. In the resultant aqueous reaction solution-impregnated composite sheet, the molar ratio of the carboxymethylating agent with glucose groups was 1.3/1.

The aqueous reaction solution-impregnated composite sheet was placed and sealed in the polyethylene bag without changing the water content of the impregnated aqueous reaction solution, and heated in the dryer at a temperature of 60° C. for 4 hours.

The resultant reacted composite sheet was rinsed and dried in the same manner as in Example 1.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

Comparative Example 4

The same procedures as in Example 1 were carried out except that the composite sheet comprising pulp fibers and polypropylene filaments intertwined with each other by a water jet entangling method, having a basis weight of 80 g/m² and impregnated with the aqueous reaction solution was heated in the dryer at 50° C. for 10 minutes, to adjust the water content in the impregnated aqueous reaction solution to 18% by weight.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

Comparative Example 5

The same procedures as in Example 1 were carried out except that the composite sheet comprising pulp fibers and polypropylene filaments intertwined with each other by a water jet entangling method, having a basis weight of 80 g/m² and impregnated with the aqueous reaction solution was heated at a temperature of 50° C. for 5 minutes in the dryer to adjust the water content in the impregnated aqueous reaction solution to 42% by weight, and then directly heated in the dryer at 50° C. for 3 hours without placing and sealing it in the polyethylene bag. After the completion of the reaction, it was found that the water content of the resultant composite sheet was zero.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

Comparative Example 6

The same composite sheet as in Example 1 comprising pulp fibers and polypropylene filaments intertwined with each other by a water jet entangling method, having a basis weight of 80 g/m² was impregnated with the same aqueous reaction solution as in Example 1 and heated in the dryer at a temperature of 50° C. for 5 minutes, to adjust the water content in the impregnated aqueous reaction solution to 42% by weight. The water content-adjusted composite sheet was rinsed and dried in the same manner as in Example 1, without applying the reaction step.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

Comparative Example 7

The same procedures as in Example 1 were carried out with the following exceptions. The composite sheet comprising pulp fibers and polypropylene filaments intertwined with each other by a water jet entangling method, and having a basis weight of 80 g/m² was impregnated with the aqueous reaction solution in an amount of 1.2 g per g of the absolute dry weight of the composite sheet. The molar ratio of the carboxymethylating agent to glucose groups was 0.52:1.

The aqueous reaction solution-impregnated composite sheet was partially dried in the dryer with the electric heater at a temperature of 50° C. for 2 minutes to adjust the water content of the impregnated aqueous reaction solution to 42% by weight, and then subjected to the same procedures as in Example 1.

The resultant cross-linked, carboxymethylated cellulose-containing composite sheet was subjected to the above-mentioned tests for the pure water absorption, the isotonic sodium chloride solution absorption and the degree of carboxymethyl group substitution.

The test results are shown in Table 1.

TABLE 1

| Item Example No. | | Impregnated aqueous reaction solution in cellulose-containing material | | Property of water-absorbent cross-linked, carboxyalkylated cellulose-containing material | | |
|---|---|---|---|---|---|---|
| | | Water content-adjusting step | Adjusted water content (% by weight) | Degree of substitution with carboxyalkyl groups | Pure water absorption (g/g) | Isotonic NaCl solution absorption (g/g) |
| Example | 1 | Applied | 42 | 0.71 | 51 | 23 |
| | 2 | Applied | 58 | 0.64 | 48 | 22 |
| | 3 | Applied | 22 | 0.50 | 38 | 20 |
| | 4 | Applied | 45 | 0.69 | 60 | 27 |
| | 5 | Applied | 33 | 0.66 | 55 | 25 |
| | 6 | Applied | 26 | 0.37 | 45 | 20 |
| Compar- | 1 | None | Unchanged | 0.35 | 28 | 14 |
| ative | 2 | None | Unchanged | 0.25 | 19 | 14 |
| Example | 3 | None | Unchanged | 0.48 | 54 | 18 |

TABLE 1-continued

| Item Example No. | | Impregnated aqueous reaction solution in cellulose-containing material | | Property of water-absorbent cross-linked, carboxyalkylated cellulose-containing material | | |
|---|---|---|---|---|---|---|
| | | Water content-adjusting step | Adjusted water content (% by weight) | Degree of substitution with carboxyalkyl groups | Pure water absorption (g/g) | Isotonic NaCl solution absorption (g/g) |
| | 4 | Applied | 18 | 0.42 | 29 | 17 |
| | 5 | Applied | 42 | 0.25 | 24 | 13 |
| | 6 | Applied | 42 | 0.11 | 20 | 13 |
| | 7 | Applied | 42 | 0.32 | 29 | 14 |

Note: (*)$_1$ . . . In Examples 1 to 6 and Comparative Examples 1 to 7, the initial water content of the impregnated reaction solution was 66.54% by weight.

As Table 1 clearly shows, the water-absorbent cross-linked, carboxyalkylated cellulose-containing materials prepared in accordance with the process of the present invention exhibited excellent pure water absorption and aqueous common salt solution absorption, and a satisfactory degree of carboxyalkyl group substitution of cellulose, namely, 0.35 to 0.8, can be obtained by only one application of the process of the present invention. Accordingly, the process of the present invention can advantageously produce the water-absorbent cross-linked, carboxyalkylated cellulose-containing material at a high efficiency and low cost, as illustrated in Examples 1 to 6.

However, as illustrated in Comparative Examples 1 and 2, in the conventional process wherein a cellulose-containing material impregnated with an aqueous reaction solution is directly heated to simultaneously cross-link and carboxyalkylate cellulose, without controlling the water content of the aqueous reaction solution impregnated in the cellulose-containing material to a specific value, the resultant cellulose derivative has low pure water absorption and aqueous common salt solution absorption. Also, as illustrated by Comparative Example 3, by employing potassium monochloroacetate having a higher solubility in water than that of sodium monochloroacetate, the aqueous reaction solution can be prepared at a low water content of 54.0% by weight (lower than 60% by weight). However, when the aqueous potassium monochloro-acetate solution is impregnated and no water content-adjusting step is applied, the resultant cellulose derivative exhibits a low aqueous common salt solution absorption, although the pure water absorption of the resultant cellulose derivative is satisfactory. Therefore, this cellulose derivative is not suitable as a water-absorbent material for ion-containing aqueous solutions.

As Comparative Example 4 illustrates, in the water content-adjusting step, if the adjusted water content of the impregnated aqueous reaction solution is too low (lower than 20% by weight), the resultant water-absorbent cellulose derivative exhibits unsatisfactory pure water absorption and ion-containing aqueous solution absorption.

Also, as Comparative Example 5 illustrates, when the simultaneous cross-linking and carboxyalkylating reaction procedure is carried out while allowing the water content of the impregnated aqueous reaction solution to decrease to a level lower than 20% by weight, the resultant cellulose derivative exhibits a low degree of substitution with the carboxyalkyl groups and significantly poor absorption of pure water and ion-containing aqueous solution.

Further, Comparative Example 6 shows that even when the water content of the impregnated aqueous reaction solution is adjusted to a suitable level, if the simultaneous cross-linking and carboxyalkylating reaction procedure is not carried out for a long enough time, the resultant cellulose derivative exhibits a low degree of substitution and poor absorption of pure water and ion-containing aqueous solutions.

Furthermore, Comparative Example 7 shows that if the amount of the aqueous reaction solution impregnated in the cellulose-containing material is too small, due to an insufficient supply of the carboxyalkylating agent, the resultant cellulose derivative exhibits a low degree of substitution and poor absorptions of pure water and ion-containing aqueous solutions.

The process of the present invention can impart a satisfactory degree of substitution with carboxyalkyl groups to cellulose by only one application of the reaction procedure. Therefore, a cross-linked, carboxyalkylated cellulose-containing material having not only a high pure water absorption but also a satisfactory ion-containing aqueous solution can be produced at a low cost and at a high efficiency by the process of the present invention.

The cross-linked, carboxyalkylated cellulose-containing material produced by the process of the present invention is widely useful, for example, as hygienic material such as disposable diapers or sanitary napkins; agricultural material such as soil water-retaining material or seedbed sheet; food-related material such as food freshness-keeping material or dehydrating material; and construction and building material such as soil-retaining material for tunneling work and water condensation-prevention sheet.

What is claimed is:

1. A process for producing a water-absorbent cross-linked, carboxyalkylated cellulose-containing material, comprising the steps of:

impregnating a cellulose-containing material with an aqueous reaction solution containing a carboxyalkylating agent, an alkali metal hydroxide, and a cross-linking agent for cellulose and having an initial water content of 50 to 90% by weight, in the impregnated aqueous reaction solution, the carboxyalkylating agent being present in a molar ratio to glucose groups of cellulose in the cellulose-containing material, of 0.7 to 2.0;

adjusting the water content of the aqueous reaction solution impregnated in the cellulose-containing material to a level of from 20 to 60% by weight and of at least 5% by weight below the initial water content, by evaporating away a portion of water from the impregnated aqueous reaction solution; and subjecting the resultant aqueous reaction solution-impregnated cellulose-containing material to a simultaneous carboxyalkylating and cross-linking reaction procedure by heating it at a temperature of 50° to 110° C., while maintaining the water content in the impregnated aqueous reaction solution at the level of 20 to 60% by weight and of at least 5% by weight below the initial water content, to convert cellulose in the cellulose-containing material to cross-linked, carboxyalkylated cellulose.

2. The process as claimed in claim 1, wherein the cellulose-containing material is selected from the group consisting of cellulose fiber materials and composite fiber materials comprising cellulose fibers and synthetic fibers.

3. The process as claimed in claim 1, wherein the cellulose-containing material is in the form of a sheet.

4. The process as claimed in claim 1, wherein the aqueous reaction solution contains 7 to 30% by weight of a carboxyalkylating agent, 2.5 to 15% by weight of an alkali metal hydroxide and 0.5 to 5% by weight of a cross-linking agent.

5. The process as claimed in claim 1, wherein the carboxyalkylating agent comprises at least one member selected from alkali metal salts of aliphatic monohaloalkylcarboxylic acids having 2 or 3 carbon atoms.

6. The process as claimed in claim 1, wherein the alkali metal hydroxide is selected from the group consisting of lithium hydroxide, potassium hydroxide, rubidium hydroxide, cesium hydroxide and sodium hydroxide.

7. The process as claimed in claim 1, wherein the cross-linking agent comprises at least one member selected from the group consisting of polyepoxy compounds, divinyl compounds, polyhalo compounds, and polyaziridinyl compounds.

8. The process as claimed in claim 1, wherein in the aqueous reaction solution, the molar ratio of the alkali metal hydroxide to the carboxyalkylating agent is 0.8 to 1.2.

9. The process as claimed in claim 1, wherein in the impregnated aqueous reaction solution, the cross-linking agent is present in an amount of 1.5 to 15% based on the weight of cellulose contained in the cellulose-containing material.

10. The process as claimed in claim 1, wherein the water content-adjusting step is carried out at a temperature of from 40° C. to 150° C. for a time not longer than 30 minutes.

11. The process as claimed in claim 1, wherein the resultant cross-linked, carboxyalkylated cellulose has a degree of substitution with carboxyalkyl groups of 0.35 to 0.8.

12. The process as claimed in claim 1, wherein the resultant cross-linked, carboxyalkylated cellulose-containing material is rinsed with a cleaning liquid comprising water and at least one water-compatible organic solvent.

* * * * *